United States Patent [19]

Griggs, III et al.

[11] 4,239,047
[45] Dec. 16, 1980

[54] METHOD AND APPARATUS FOR AURALLY DETERMINING PRESENCE OR ABSENCE OF PATHOLOGICAL STENOSIS

[75] Inventors: William L. Griggs, III; Ernest E. Serrano; Dan Page; Charles G. Reul, all of Fort Smith, Ark.

[73] Assignee: William L. Griggs, III, Fort Smith, Ark.

[21] Appl. No.: 908,159

[22] Filed: May 22, 1978

[51] Int. Cl.³ .............................................. A61B 5/02
[52] U.S. Cl. ................................ 128/663; 73/861.25
[58] Field of Search .......... 128/2 R, 2 S, 2 Z, 2.05 F, 128/2.05 Z, 2.1 R, 24 A, 2.05 S, 630, 194 A, 663, 715; 340/3 D; 73/194 A; 179/1 N, 1 ST, 107 R

[56] References Cited
U.S. PATENT DOCUMENTS

| | | | |
|---|---|---|---|
| 3,171,406 | 3/1965 | Baum et al. | 128/2.05 S |
| 3,430,625 | 3/1969 | McLeod | 128/24 A |
| 3,577,981 | 5/1971 | Kuris | 128/2 V |
| 3,710,792 | 1/1973 | Light | 128/663 |
| 3,732,532 | 5/1973 | Flaherty et al. | 128/2.05 F X |
| 3,732,868 | 5/1973 | Willems et al. | 128/2.06 A X |
| 3,848,091 | 11/1974 | Stearns et al. | 128/2 Z |
| 4,109,106 | 8/1978 | Voss | 179/1 N |
| 4,109,642 | 8/1978 | Reid et al. | 128/663 |
| 4,154,231 | 5/1979 | Russell | 128/663 |

FOREIGN PATENT DOCUMENTS 524549  2/1969  U.S.S.R. ............................. 128/2 Z

OTHER PUBLICATIONS

Borodzinski, K. et al., "Quantitative Transcutaneous Measurements of Blood Flow in Carotid Artery by Means of Pulse and CW Doppler Methods," Ultrasound in Med. & Biol., vol. 2 No. 3, Jun. 1976, pp. 189-193.

Satomura, S., "UTS Doppler Method for Inspection of Cardiac Functions", Jrnl. Ac. Soc. of America, vol. 29 No. 11, Nov. 1979, pp. 1181-1185.

Primary Examiner—Robert W. Michell
Assistant Examiner—Francis J. Jaworski
Attorney, Agent, or Firm—Rogers, Eilers & Howell

[57]  ABSTRACT

A Doppler scan is made of a person's blood vessels, a recording is made of the resulting plural-frequency sounds, and then successive aural sensings of selected frequency-range portions of that Doppler scan recording are made.

15 Claims, 5 Drawing Figures

METHOD AND APPARATUS FOR AURALLY DETERMINING PRESENCE OR ABSENCE OF PATHOLOGICAL STENOSIS

BACKGROUND OF THE INVENTION

It has been suggested that a visual analysis of the graphical output of a spectrum recording machine can be used to determine the presence or absence of pathological stenosis. More particularly, it has been suggested that waves can be directed toward a blood vessel, that a spectrum recording machine can be used to develop a graphical output representing the resulting plural-frequency response, and that a visual analysis can be made of that portion of that graphical output which is in the five kilohertz to twelve kilohertz range to determine the presence or absence of pathological stenosis. However, the use of visual analyses of the graphical outputs of spectrum recording machines is slow, indirect, expensive and difficult. It has also been suggested that sounds which are developed by a continuous wave, directional Doppler Flow Meter can be sensed aurally to determine the presence or absence of pathological stenosis. However, some difficulties have been experienced in using such sounds to make such determinations.

SUMMARY OF THE INVENTION

The present invention provides a method and apparatus for making accurate aural determinations of the presence or absence of pathological stenosis. In that method, a Doppler scan is made of a person's blood vessels, a recording is made of the resulting plural-frequency sounds, and then that portion of those plural frequency sounds which is in the range of one hertz to five and one-half kilohertz is sensed aurally to detect any sounds that are not present in the Doppler scan recordings of blood vessels which are not stenotic. If any such sounds are detected, that portion of the recorded plural-frequency sounds which is in the range of four kilohertz to five and one-half kilohertz is sensed aurally to detect sounds which could be due to pathological stenosis. If that second aural sensing clearly indicates the presence of pathological stenosis in a given portion of an artery, and if no vein is close enough to that portion of that artery to permit venous artifacts to be a substantial part of the plural-frequency sounds in the Doppler scan recording, no further aural checking is needed. However, if a vein was close enough to the sensed portion of the artery to permit venous artifacts to be a substantial part of the plural-frequency sounds in the Doppler scan recording, that portion of the recorded plural-frequency sounds which is in the range of one kilohertz to five and one-half kilohertz will be sensed aurally to determine whether venous artifacts as well as sounds due to pathological stenosis are in the recorded plural-frequency sounds. If that third aural sensing indicates that no venous artifacts are present in the recorded plural-frequency sounds, no further aural checking is needed. However, if venous artifacts are present, further aural sensings of those portions of the recorded plural-frequency sounds which are in the ranges of four to five and one-half kilohertz and of one to five and one-half kilohertz will be made until the analyst is convinced that a pathological stenosis is or is not present. It is, therefore, an object of the present invention to provide a method of accurately determining the presence or absence of pathological stenosis by making successive aural sensings of selected frequency-range portions of a Doppler scan recording of a person's blood vessels.

An audio aid, which includes a plurality of high-pass audio filters, can selectively and individually connect those filters in series relation between the source of the recorded plural-frequency sounds and a sound reproducing device. High-pass audio filters, with stop-band rejections as high as fifty to sixty decibels that begin within about one-quarter of an octave below the cutoff frequency, have been found to be useful. Those high-pass audio filters can be used to select those portions of the recorded plural-frequency sounds that will be made audible by the sound reproducing device. It is, therefore, an object of the present invention to provide an audio aid, for use in aural determinations of the presence or absence of pathological stenosis, which includes a plurality of high-pass audio filters that have stop-band rejections as high as fifty to sixty decibels which begin within about one-quarter of an octave below the cutoff frequency, and which selectively and individually connects those filters in series relation between the source of the recorded plural-frequency sounds and a sound reproducing device.

Each of the high-pass audio filters of the audio aid provided by the present invention is intended to attenuate signals below the cutoff frequency thereof to a level of virtual inaudibility. However, each of those filters must pass frequencies above that cutoff frequency with little or no attenuation. It is, therefore, an object of the present invention to provide an audio aid, for use in aural determinations of the presence or absence of pathological stenosis, that has high-pass audio filters which attenuate signals below the cutoff frequencies thereof to a level of virtual inaudibility and yet pass frequencies above that cutoff frequency with little or no attenuation.

The audio aid provided by the present invention is made with a reasonably-high level of input impedance. As a result, that filter aid will not overload any appropriate signal source to which it is connected; and hence it can be used with signal sources that utilize magnetic tapes of Doppler Imaging equipment, other magnetic tapes, phonograph records or other sound recordings. It is, therefore, an object of the present invention to provide an audio aid which has a reasonably-high level of input impedance.

The audio aid of the present invention is provided with a hiss filter that can be selectively connected in series with each of the high-pass audio filters of that audio aid. That hiss filter makes it possible to use that audio aid with signal sources which use magnetic tapes or other sound recordings that tend to generate or reproduce hiss frequencies. However, that hiss filter could be bypassed where the audio aid was used with a signal source that used a sound recording which did not generate or reproduce hiss frequencies. It is, therefore, an object of the present invention to provide an audio aid which has a hiss filter that can be selectively connected in series with each of the high-pass audio filters thereof.

The audio aid provided by the present invention can selectively bypass all of the high pass filters thereof; and hence the sound reproducing device for that audio aid can selectively supply an unfiltered output as well as variously-filtered outputs. As a result, a comparison can easily be made between the signal which is supplied to the audio aid and a filtered version of that signal. It is, therefore, an object of the present invention to provide an audio aid which has a plurality of high-pass audio filters and also has a bypass circuit which enables a signal that is applied to that audio aid to be compared with a filtered version of that signal.

The audio aid provided by the present invention develops essentially the same magnitude of output whether the signal which is supplied to that audio aid passes through the bypass circuit thereof or through one of the high-pass audio filters thereof. That audio aid attains that result by providing equalizer circuits which enable that bypass circuit and all of those high-pass audio filters to develop essentially the same amplitudes for the outputs thereof within their individual pass bands. In addition, those equalizer circuits constitute load impedances which tend to improve the performance and efficiency of those high-pass audio filters. It is, therefore, an object of the present invention to provide an audio aid with equalizer circuits, in the bypass circuit and high-pass audio filter circuits thereof, which will permit the magnitude of the output signal of that audio aid to be essentially constant and which will constitute load impedances that tend to improve the efficiency of those high-pass audio filters.

Other and further objects and advantages of the present invention should become apparent from an examination of the drawing and accompanying description.

In the drawing and accompanying description a preferred embodiment of the present invention is shown and described but it is to be understood that the drawing and accompanying description are for the purpose of illustration only and do not limit the invention and that the invention will be defined by the appended claims.

DETAILED DESCRIPTION OF PREFERRED EMBODIMENT

Figure 1:
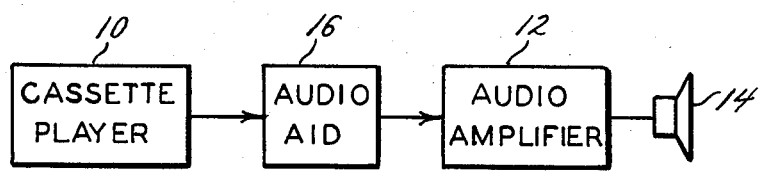
FIG. 1 is a block diagram of an audio aid which is connected to the output of a cassette player and which has its output connected to an audio amplifier that supplies signals to a speaker.
Figure 2:
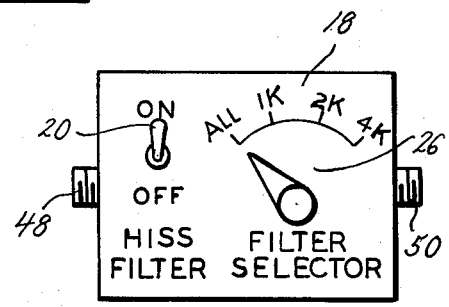
FIG. 2 is a front elevational view of the panel of the audio aid of FIG. 1.
Figure 3:
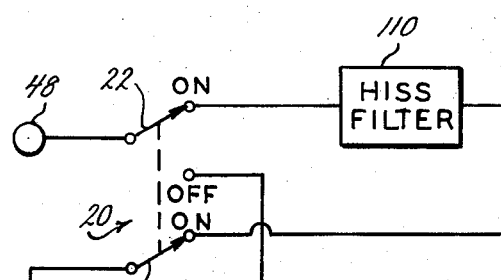
FIG. 3 is a schematic diagram of one preferred embodiment of the audio aid of FIG. 1.

Referring particularly to the drawing, the numeral 10 denotes a cassette player of standard and usual kind which can serve as a signal source. The numeral 12 denotes an adjustable gain audio amplifier of standard and usual design, and the numeral 14 denotes a speaker of standard and usual design. The numeral 16 generally denotes one preferred embodiment of audio aid which is provided by the present invention; and that audio aid receives signals from the cassette player 10 and supplies signals to the audio amplifier 12. That audio aid has a panel 18 with a Hiss Filter switch 20 and with a rotatable Filter Selector switch 26. As shown by FIG. 3, switch 20 has ganged movable contacts 22 and 24 that can be set in "ON" or "OFF" positions. Also as shown by FIG. 3, the switch 26 has two ganged movable contacts 28 and 30 and four sets of stationary contacts 32 and 34, 36 and 38, 40 and 42, and 44 and 46. An input jack 48 is provided at the left-hand side of panel 18, and an output jack 50 is provided at the right-hand side of that panel.

An equalizer circuit is connected between stationary contacts 32 and 34; and it consists of three one kilohm carbon potentiometers 52, 54 and 56 that are connected as adjustable resistors. Potentiometers 52 and 56 are connected in series between contacts 32 and 34, and potentiometer 54 is connected between ground and the junction of those two potentiometers. The numeral 58 denotes a one kilohertz high-pass filter which has the input thereof connected to stationary contact 36. An equalizer circuit is connected between the output of that filter and stationary contact 38; and it consists of three one kilohm carbon potentiometers 60, 62 and 64 that are connected as adjustable resistors. Potentiometers 60 and 62 are connected in series between the output of filter 58 and stationary contact 38, and potentiometer 64 is connected between ground and the junction between potentiometers 60 and 62. The numeral 66 denotes a two kilohertz high-pass filter which has the input thereof connected to stationary contact 40. An equalizer circuit is connected between the output of that filter and stationary contact 42; and it consists of three one kilohm carbon potentiometers 68, 70 and 72. Potentiometers 68 and 70 are connected in series between the output of filter 66 and stationary contact 42; and potentiometer 72 is connected between ground and the junction between potentiometers 68 and 70. The numeral 74 denotes a four kilohertz high-pass filter which has the input thereof connected to stationary contact 44. An equalizer circuit is connected between the output of that filter and stationary contact 46; and it consists of three one kilohm carbon potentiometers 76, 78 and 80. Potentiometers 76 and 78 are connected in series between the output of filter 74 and contact 46; and potentiometer 80 is connected between ground and the junction between potentiometers 76 and 78. A resistor 82 is connected between ground and the junction between movable contact 30 and jack 50. The equalizer circuit, which consists of potentiometers 52, 54 and 56, is part of a bypass circuit which can cause the signal at movable contact 28 to bypass all of the filters 58, 66 and 74.

The numeral 110 denotes a Hiss Filter which is connected in series between the "ON" contacts of switch 20. Whenever that switch is in its "ON" position, that Hiss Filter will be connected in series between input jack 48 and movable contact 28 of Filter Selector switch 26. However, when switch 20 is in its "OFF" position, a direct metallic path from input jack 48 to movable contact 28 bypasses that Hiss Filter.

Figure 4:
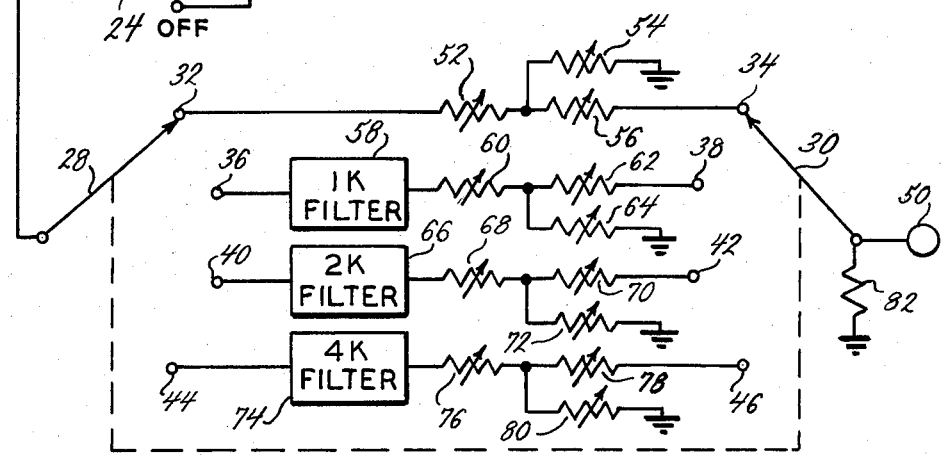
FIG. 4 is a schematic diagram of the circuit for three of the filters of FIG. 3, and, FIG. 5 is a schematic diagram of the hiss filter of FIG. 3.
Figure 4:
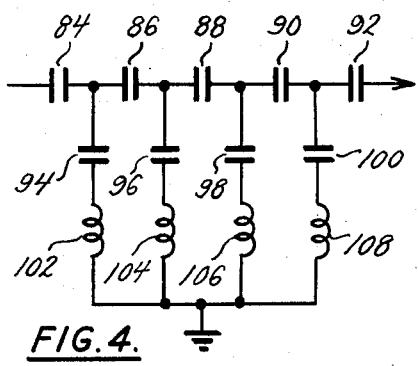

Referring particularly to FIG. 4, the numerals 84, 86, 88, 90, 92, 94, 96, 98 and 100 denotes capacitors; and the numerals 102, 104, 106 and 108 denote inductors. Those capacitors and inductors are connected to constitute a multi-pole elliptic passive filter which acts as a high-pass filter. By selecting the values set out hereinafter in CHART I, the filter of FIG. 4 can be used as the high-pass filter 58, the high-pass filter 66 or the high-pass filter 74.

The capacitors 84, 86, 88, 90 and 92 are connected in series between the input and output of the high-pass filter of FIG. 4; and capacitor 94 and inductor 102 constitute a series-resonant tuned circuit connected between ground and the junction between capacitors 84 and 86. Capacitor 96 and inductor 104 constitute a second series-resonant tuned circuit connected between ground and the junction between capacitors 86 and 88.

Capacitor 98 and inductor 106 constitute a third series-resonant tuned circuit connected between ground and the junction between capacitors 88 and 90; and capacitor 100 and inductor 108 constitute a fourth series-resonant tuned circuit connected between ground and the junction between capacitors 90 and 92.

Figure 5:
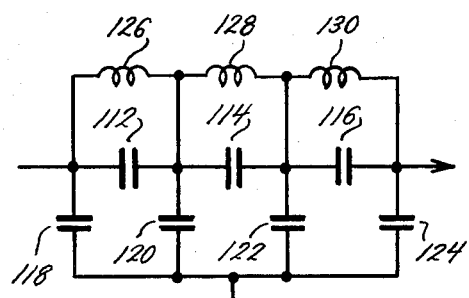

Referring particularly to FIG. 5, the numerals 112, 114, 116, 118, 120, 122 and 124 denote capacitors, and the numerals 126, 128 and 130 denote inductors. Those capacitors and inductors are connected to constitute a low-pass filter which can be used as the Hiss Filter 110.

The capacitor 112 and the inductor 126 constitute a parallel-resonant tuned circuit, the capacitor 114 and inductor 128 constitute a second parallel-resonant tuned circuit, and the capacitor 116 and inductor 130 constitute a third parallel-resonant tuned circuit. Those parallel-resonant tuned circuits are connected in series between the input and output of the Hiss Filter 110. Capacitor 118 is connected between ground and the input of that Hiss Filter, capacitor 120 is connected between ground and the junction between the first and second parallel-resonant tuned circuits, the capacitor 122 is connected between ground and the junction between the second and third parallel resonant tuned circuits, and the capacitor 124 is connected between ground and the output of that Hiss Filter. Where the capacitors and inductors of FIG. 5 are given the values in CHART II, the Hiss Filter acts as a low-pass filter which has a frequency of five and one half kilohertz.

CHART I

| Number of Capacitor | Microfarads For 1 Kilohertz | Microfarads For 2 Kilohertz | Microfarads For 4 Kilohertz |
|---|---|---|---|
| 84 | 0.128 | 0.0639 | 0.032 |
| 86 | 0.0955 | 0.0478 | 0.0239 |
| 88 | 0.13 | 0.065 | 0.0325 |
| 90 | 0.117 | 0.058 | 0.029 |
| 92 | 0.162 | 0.081 | 0.0405 |
| 94 | 1.29 | 0.643 | 0.322 |
| 96 | 0.209 | 0.104 | 0.0522 |
| 98 | 0.154 | 0.0768 | 0.0384 |
| 100 | 0.341 | 0.17 | 0.0852 |

| Number of Inductor | Henries For 1 Kilohertz | Henries For 2 Kilohertz | Henries For 4 Kilohertz |
|---|---|---|---|
| 102 | 0.125 | 0.0624 | 0.0312 |
| 104 | 0.184 | 0.0918 | 0.0459 |
| 106 | 0.219 | 0.109 | 0.0547 |
| 108 | 0.165 | 0.0825 | 0.0412 |

CHART II

| Number of Capacitor | Microfarads For 5.5 Kilohertz |
|---|---|
| 112 | 0.0059 |
| 114 | 0.031 |
| 116 | 0.0217 |
| 118 | 0.034 |
| 120 | 0.043 |
| 122 | 0.036 |
| 124 | 0.0236 |

| Number of Inductor | Millihenries For 5.5 Kilohertz |
|---|---|
| 126 | 34.32 |
| 128 | 20.24 |
| 130 | 22.6 |

All of the capacitors in CHARTS I and II have capacitance values in microfarads and have tolerances in the range of one percent. All of the inductors in those CHARTS have inductance values in the range of Henries or Millihenries and have tolerances in the range of one percent.

The filters 58, 66 and 74 constitute high-pass filters which have stop-band rejections as high as fifty to sixty decibels which begin within about one quarter octave below the chosen cutoff frequency. However, those filters will pass frequencies that are above the cut-offs thereof with little or no attenuation. Because those three filters use passive elements, they are extremely stable and reliable; and hence they enable the audio aid to provide highly accurate analyses of audio signals. If desired, a chebyshev filter could be substituted for the filter shown in FIG. 4. Further, if desired, high quality active filters could be used in place of the multi-pole elliptic passive filter shown in FIG. 4.

The equalizer circuits of FIG. 3 are intended to perform two functions; namely, to standardize the load impedances which the outputs of the filters 58, 66 and 74 will "see," and to make the amplitudes of the signals, which are applied to the output jack 50, be the same regardless of which position the movable contacts 28 and 30 of the Filter Selector switch 26 occupy. To set those equalizer circuits so they can perform those two functions, an audio generator of standard design will be connected to the input jack 48 and a sensitive voltmeter of standard design will be connected to the output jack 50. That audio generator will be set to provide a signal which has a frequency that will pass through all of the filters 58, 66 and 74; and one such signal is a sine wave that has a frequency greater than four kilohertz but less than five and one-half kilohertz. The audio generator will be set to provide an output that has a voltage value of a few tenths of a volt.

The movable contacts 28 and 30 of the Filter Selector switch 26 will be set in their ALL positions wherein they engage stationary contacts 32 and 34 respectively; and then the movable contacts of the potentiometers 52, 54 and 56 will be set to provide a signal at output jack 50 which has an amplitude that is about eighty percent of the amplitude of the signal which is applied to input jack 48. Thereafter, the movable contacts 28 and 30 of the Filter Selector switch 26 will be successively set in their 1K, 2K and 4K positions wherein they engage stationary contacts 36 and 38, 40 and 42, and 44 and 46 respectively; and, in each of those positions, the appropriate potentiometers of the equalizer circuits will be set to standardize the load impedances which the outputs of the filters 58, 66 and 74 will "see" and also to make the amplitudes of the signals, which are applied to the output jack 50, be essentially the same as that which was set when the Filter Selector switch was in its ALL position.

The audio aid provided by the present invention can have the input jack 48 thereof connected to that external jack of the cassette player 10 which normally is connected to an external amplifier and speaker. As a result, that audio aid can be used with cassette players which are available in most clinics and in most hospitals which use Doppler Imaging equipment. The output of that audio aid can be connected to a variable gain audio amplifier 12 of the type commonly used in clinics and hospitals which use Doppler Imaging Equipment; and the output of that amplifier is connected to a speaker of the type commonly found in such clinics and hospitals.

The audio aid provided by the present invention is particularly useful in analyzing the Doppler sounds which are developed by use of a continuous wave, directional Doppler Flow Meter that is currently marketed by the Carolina Medical Electronics Company under the trade name DOPSCAN. Those Doppler sounds are preserved in the form of magnetic tapes in cassettes. Those Doppler sounds are infinitely more complex than pure tones; and some of the stenosis-indicating components of those sounds have smaller amplitudes than some of the less-significant components of those sounds. Further, harmonics of various components of those sounds plus hissing sounds, which are inherently produced by the magnetic tapes of cassette players, tend to mask some of the stenosis-indicating relatively low-amplitude Doppler sounds.

In using the audio aid provided by the present invention, the analyst could, if he desired, set the Hiss Filter switch 20 in the "OFF" position; and, where that was done, audio signals corresponding to all of the Doppler sounds and harmonics thereof and corresponding to all hissing sounds would bypass the Hiss Filter 110 and be applied to the movable contact 28 of the Filter Selector switch 26. However, because the harmonics of the Doppler sounds and the hissing sounds produced by the magnetic tape tend to overshadow the stenosis-indicating relatively, low-amplitude Doppler sounds, the Hiss Filter switch 26 will usually be left in the "on" position.

The analyst will set the Filter Selector switch 26 in the ALL position, operate the cassette player 10, and then listen to the sounds from the speaker 14. Those sounds can be in the range of one hertz to five and one-half kilohertz. If the analyst does not detect any sounds which are not present in the Doppler scan recording of blood vessels that are not stenotic, he or she can conclude, with a considerable degree of assurance, that the blood vessels of the person in question are not stenotic. To double check that initial conclusion, the analyst can shift the Filter Selector switch 26 to its 4K position, re-wind the magnetic tape, re-start the cassette player 10, and again listen to the sounds from the speaker 14. Those sounds will have essentially all components thereof which are below four kilohertz filtered out, so the sounds heard by the analyst will be between four kilohertz and five and one-half kilohertz. If the analyst does not hear any sounds which are not present in the Doppler scan recording of blood vessels that are not stenotic, he or she can be substantially-completely certain that the blood vessels of the person in question are not stenotic.

On the other hand if, when the Filter Selector switch 26 is in its ALL position and the cassette player 10 is operated, the analyst detects any sounds which are not present in the Doppler scan recording of blood vessels that are not stenotic, the analyst will be alerted to the fact that there is a possible stenotic condition in the blood vessels of the person in question. Thereupon, the analyst will shift the Filter Selector switch 26 to its 4K position, re-wind the magnetic tape, re-start the cassette player 10, and again listen to the sounds from the speaker 14. If a stenotic condition exists in the person's blood vessels, stenosis-indicating Doppler sounds will develop in the range of four kilohertz to five and one-half kilohertz. By filtering out all sounds below four kilohertz, the four kilohertz high-pass filter 74, will permit those stenosis-indicating Doppler sounds to be heard even though they are of relatively low-amplitude.

If the analyst detects stenosis-indicating Doppler sounds when the Filter Selector switch 26 is in the ALL position, and also senses such sounds when that switch is in its 4K position, he or she can be substantially-completely certain that a stenosis exists in the blood vessels of the person in question; unless those stenosis-indicating Doppler sounds were sensed in an artery which was close to a vein that could develop venous artifacts in the four kilohertz to five and one-half kilohertz range. In the latter event, the analyst would set the Filter Selector switch 26 in its 1K position, re-wind the magnetic tape, re-start the cassette player 10, and again listen to the sounds from the speaker 14. If the stenosis-indicating Doppler sounds, which the analyst heard when the Filter Selector switch 26 was in its ALL and 4K positions, were due, in whole or in part, to venous artifacts, the analyst would hear a "blowing" sound when he or she listened to the sounds from speaker 14 while the Filter Selector switch 26 was in its 1K position.

By recurrently listening to the sounds from the speaker 14, as the magnetic tape is recurrently re-wound and "played"—sometimes with the Filter Selector switch 26 in its 4K position and sometimes with that switch in its 1K position, the analyst is able to determine whether the stenosis-indicating Doppler sounds are due wholly to venous artifacts or also due to stenosis. When that switch is set in its 4K position, most sounds due to venous artifacts will be filtered out, so the analyst will be able to hear any stenosis-indicating sounds, even though they are of relatively low-amplitude.

The 2K position for the Filter Selector switch 26 would be useful in the event the audio aid were to be used with a continuous wave, directional Doppler Flow Meter of some other type which tended to permit an undue amount of low-frequency sound to be reproduced by the speaker 14 when that switch was in its 1K position. Also, if that audio aid were to be used with a continuous wave, directional Doppler Flow Meter that produced stenosis-indicating Doppler sounds in a frequency range other than four to five and one-half kilohertz, the components of the high-pass filter 74 could be changed to establish a stop-band other than the four kilohertz stop-band established for the filter 74. Further, if that audio aid were to be used with a pulse-type, directional Doppler Flow Meter, and if the resulting stenosis-indicating Doppler sounds were in a frequency range other than four to five and one-half kilohertz, the components of the high-pass filter 74 could be changed to establish a stop-band other than the four kilohertz stop-band established for the filter 74. Importantly, the audio aid of the present invention makes it possible for an analyst to aurally sense a wide sound spectrum which includes most potentially-significant Doppler sounds, and then aurally sense specific portions of that sound spectrum to determine, with a hitherto-unattainable accuracy, the presence or absence of stenosis-indicating sounds. The cutoff frequencies of the 1K, 2K and 4K filters progress from one to the other by one octave; and, by sequentially shifting the knob of Filter Selector switch 26 to and through its 1K, 2K and 4K positions, the analyst can select stop-bands that are spaced one octave apart.

The hiss, that is inherent in the use of present day magnetic tape cassettes, makes it desirable to filter out all sounds above five and one-half kilohertz. However, in the event unusually-high fidelity tapes, or some other form of unusually-high fidelity recordings, were to be used, the upper limit of the stop-band of the Hiss Filter 110 could be raised. Importantly, the filtering provided by that filter, as well as the filtering provided by the 1K, 2K and 4K filters 58, 66 and 74, should be of an abrupt nature and should be substantially-complete. Where that is done, all frequency components below each stop band will be substantially-completely filtered out with little or no attenuation of frequency components above that stop band.

If desired, a blocking capacitor could be built into the audio aid 16 between the input jack 48 and the movable contact 22 of the Hiss Filter Switch 20. That blocking capacitor would prevent the flow of all undesired direct current. To keep that blocking capacitor from blocking the flow of desired low frequency contents of the signal from the cassette player 10, that blocking capacitor should have a capacitance value of about one microfarad.

Whereas the drawing and accompanying description have shown and described a preferred embodiment of the present invention, it should be apparent to those skilled in the art that various changes may be made in the form of the invention without affecting the scope thereof.

What we claim is:

1. The method of aurally determining the presence or absence of pathological stenosis in a person's blood vessels which comprises making a sound recording of the plural-frequency sounds that are developed by a Doppler scan of said blood vessels, using said sound recording and a filter with a predetermined rejection frequency to develop electrical signals within a predetermined frequency range which can be used to aurally reproduce any stenosis-indicating sounds of a given frequency in said plural-frequency sounds, and thereafter using said sound recording and a different filter with a different predetermined rejection frequency to develop electrical signals within a different predetermined frequency range which can be used to aurally reproduce any stenosis-indicating sounds of a different frequency in said plural-frequency sounds, to make successive aural sensings of different-frequency portions of said plural-frequency sounds that are developed by said Doppler scan by making successive aural sensings of different frequency ranges of said recorded plural-frequency sounds, thereby facilitating the detecting of some hard-to-detect stenosis-indicating sounds.

2. The method of aurally determining the presence or absence of pathological stenosis in a person's blood vessels which comprises making a sound recording of the plural-frequency sounds that are developed by a Doppler scan of said blood vessels, using said sound recording and a filter with a predetermined rejection frequency to develop electrical signals within a predetermined frequency range which can be used to aurally reproduce any stenosis-indicating sounds of a given frequency in said plural-frequency sounds, and thereafter using said sound recording and a different filter with a different predetermined rejection frequency to develop electrical signals within a different predetermined frequency range which can be used to aurally reproduce any stenosis-indicating sounds of a different frequency in said plural-frequency sounds, to make successive aural sensings of different-frequency portions of said plural-frequency sounds that are developed by said Doppler scan by making successive aural sensings of different frequency ranges of said recorded plural-frequency sounds, thereby facilitating the detecting of some hard-to-detect stenosis-indicating sounds, one of said aural sensings being in the frequency range wherein stenosis-indicating sounds are most likely to be sensed.

3. The method of aurally determining the presence or absence of pathological stenosis in a person's blood vessels which comprises making a sound recording of the plural-frequency sounds that are developed by a Doppler scan of said blood vessels, using said sound recording and a filter with a predetermined rejection frequency to develop electrical signals within a predetermined frequency range which can be used to aurally reproduce any stenosis-indicating sounds of a given frequency in said plural-frequency sounds, and thereafter using said sound recording and a different filter with a different predetermined rejection frequency to develop electrical signals within a different predetermined frequency range which can be used to aurally reproduce any stenosis-indicating sounds of a different frequency in said plural-frequency sounds, to make successive aural sensings of different-frequency portions of said plural-frequency sounds that are developed by said Doppler scan by making successive aural sensings of different frequency ranges of said recorded plural-frequency sounds, thereby facilitating the detecting of some hard-to-detect stenosis-indicating sounds, one of said aural sensings being in the frequency range wherein venous artifacts can be sensed.

4. The method of aurally determining the presence or absence of pathological stenosis in a person's blood vessels which comprises making a sound recording of the plural-frequency sounds that are developed by a Doppler scan of said blood vessels, using said sound recording and a filter with a predetermined rejection frequency to develop electrical signals within a predetermined frequency range which can be used to aurally reproduce any stenosis-indicating sounds of a given frequency in said plural-frequency sounds, and thereafter using said sound recording and a different filter with a different predetermined rejection frequency to develop electrical signals within a different predetermined frequency range which can be used to aurally reproduce any stenosis-indicating sounds of a different frequency in said plural-frequency sounds, to make successive aural sensings of different-frequency portions of said plural-frequency sounds that are developed by said Doppler scan by making successive aural sensings of different frequency ranges of said recorded plural-frequency sounds, thereby facilitating the detecting of some hard-to-detect stenosis-indicating sounds, one of said aural sensings being in the frequency range wherein stenosis-indicating sounds are most likely to be sensed, another of said aural sensings being in the frequency range wherein venous artifacts can be sensed.

5. The method of aurally determining the presence or absence of pathological stenosis in a person's blood vessels which comprises making a sound recording of the plural-frequency sounds that are developed by a Doppler scan of said blood vessels, using said sound recording and a filter with a predetermined rejection frequency to develop electrical signals within a predetermined frequency range which can be used to aurally reproduce any stenosis-indicating sounds of a given frequency in said plural-frequency sounds, and thereafter using said sound recording and a different filter with a different predetermined rejection frequency to develop electrical signals within a different predetermined frequency range which can be used to aurally reproduce any stenosis-indicating sounds of a different frequency in said plural-frequency sounds, to make successive aural sensings of different-frequency portions of said plural-frequency sounds that are developed by said Doppler scan by making successive aural sensings of different frequency ranges of said recorded plural-frequency sounds, thereby facilitating the detecting of some hard-to-detect stenosis-indicating sounds, the first said and said different predetermined frequency ranges being obtained by the abrupt and substantially-complete filtering out of sounds below said first said and said different predetermined frequency ranges, respectively.

6. The method of aurally determining the presence or absence of pathological stenosis in a person's blood vessels which comprises making a sound recording of the plural-frequency sounds that are developed by a Doppler scan of said blood vessels, using said sound recording and a filter with a predetermined rejection frequency to develop electrical signals which are within a predetermined frequency range and which have had components of said plural-frequency sounds that could be due to hiss and to harmonics filtered out and which can be used to aurally reproduce any stenosis-indicating sounds of a given frequency in said plural-frequency sounds, and thereafter using said sound recording and a different filter with a different predetermined rejection frequency to develop electrical signals within a different predetermined frequency range, wherein stenosis-indicating sounds are most likely to be sensed which can be used to aurally reproduce any stenosis-indicating sounds of a different frequency in said plural-frequency sounds, to make successive aural sensings of different-frequency portions of said plural-frequency sounds that are developed by said Doppler scan by making successive aural sensings of different frequency ranges of said recorded plural-frequency sounds, thereby facilitating the detecting of some hard-to-detect stenosis-indicating sounds.

7. The method of claim 6 wherein the frequencies of said hiss sounds and of said harmonics are dominantly above five and one-half kilohertz, and wherein one of said predetermined frequency ranges is four kilohertz to five and one-half kilohertz.

8. An audio aid which facilitates aural sensing of Doppler scan signals and which comprises an input that is connectable to a source of Doppler scan signals, an output which is connectable to a sound reproducing system, a plurality of high-pass filters that have different rejection frequencies within the frequency spectrum of said Doppler scan signals, and selection means which can selectively connect each of said high-pass filters between said input and said output to facilitate selection of different-frequency portions of said Doppler scan signals that are to be supplied to said sound reproducing system to be converted into audible sounds, said audio aid being adapted, in one setting of said selection means, to pass stenosis-indicating signals of relatively low amplitude and to block lower-frequency signals of higher amplitudes.

9. An audio aid as claimed in claim 8 wherein said selection means can connect a bypass circuit between said input and said output while disconnecting all of said high-pass filters from said input and said output, whereby said audio aid can selectively supply to said output signals that have unaltered-frequency content or altered-frequency content.

10. An audio aid as claimed in claim 8 wherein a low-pass filter, which has a frequency above the frequencies of all of said high-pass filters, is selectively connectable in series relation with any of said high-pass filters to sharply attenuate high frequency contents of the signal from said signal source.

11. An audio aid as claimed in claim 8 wherein said high-pass filters have stop-band rejections in the range of tens of decibels which begin less than one octave below the cutoff frequencies of said high-pass filters.

12. An audio aid as claimed in claim 8 wherein equalizer circuits are connected in series relation between the outputs of said high-pass filters and said output, and wherein said equalizer circuits are adapted to make the amplitudes of the signals which said high-pass filters apply to said output be substantially equal.

13. An audio aid as claimed in claim 8 wherein said selection means can connect a bypass circuit between said input and said output while disconnecting all of said high-pass filters from said input and said output, wherein equalizer circuits are connected in series relation between the outputs of said bypass circuit and of said high-pass filters, and wherein said equalizer circuits are adapted to make the amplitudes of the signals which said bypass circuit and said high-pass filters apply to said output be substantially equal.

14. The combination of a source of Doppler scan signals which provides electrical signals that correspond to plural-frequency sounds which are developed by a Doppler scan of the blodd vessels of a person, an audio aid which facilitates aural sensing of Doppler scan signals and which comprises an input that is connectable to a source of Doppler scan signals, an output which is connectable to a sound reproducing system, a plurality of high-pass filters that have different rejection frequencies within the frequency spectrum of said Doppler scan signals, and selection means which can selectively connect each of said high-pass filters between said input and said output to facilitate selection of different-frequency portions of said Doppler scan signals that are to be supplied to said sound reproducing system to be converted into audible sounds, said audio aid being adapted, in one setting of said selection means, to pass stenosis-indicating signals of relatively low amplitude and to block lower-frequency signals of higher amplitudes, said source of Doppler scan signals being a magnetic tape containing Doppler sounds, an amplifier and a speaker which are parts of said sound-reproducing system, said high-pass filters having cut off frequencies that are specifically different from each other, all of said cutoff frequencies being below five kilohertz.

15. The combination of a source of Doppler scan signals which provides electrical signals that correspond to plural-frequency sounds which are developed by a Doppler scan of the blood vessels of a person, an audio aid which has an input that is connectable to said source of Doppler scan signals, a sound reproducing system including an audio amplifier and a speaker, an output of said audio aid which is connected to said sound reproducing system, a plurality of high-pass filters in said audio aid which have different rejection frequencies, and selection means in said audio aid which can selectively connect each of said high-pass filters between said input and said output, said audio aid being adapted, in one setting of said selection means, to pass stenosis-indicating signals of relatively low amplitudes and to block lower-frequency signals of higher amplitudes, said high-pass filters having cutoff frequencies that are specifically different from each other.

\* \* \* \* \*